US010799637B2

(12) United States Patent
Helmer

(10) Patent No.: US 10,799,637 B2
(45) Date of Patent: *Oct. 13, 2020

(54) CARTRIDGE CARRIER ASSEMBLY

(71) Applicant: Sanofi-Aventis Deutschland GMBH, Frankfurt am Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 90 days.

This patent is subject to a terminal disclaimer.

(21) Appl. No.: 15/773,297

(22) PCT Filed: Nov. 2, 2016

(86) PCT No.: PCT/EP2016/076463
§ 371 (c)(1),
(2) Date: May 3, 2018

(87) PCT Pub. No.: WO2017/076925
PCT Pub. Date: May 11, 2017

(65) Prior Publication Data
US 2018/0318509 A1 Nov. 8, 2018

(30) Foreign Application Priority Data
Nov. 5, 2015 (EP) .................................... 15193195

(51) Int. Cl.
*A61M 5/24* (2006.01)
*A61M 5/20* (2006.01)
(Continued)

(52) U.S. Cl.
CPC ........ *A61M 5/2466* (2013.01); *A61M 5/2033* (2013.01); *A61M 5/24* (2013.01);
(Continued)

(58) Field of Classification Search
CPC .... A61M 5/24; A61M 5/3287; A61M 5/2466; A61M 5/3202; A61M 2005/247
See application file for complete search history.

(56) References Cited

U.S. PATENT DOCUMENTS

| 3,820,652 A | 6/1974 | Thackston |
| 4,303,069 A | 12/1981 | Cohen |
| (Continued) | | |

FOREIGN PATENT DOCUMENTS

| CN | 102036711 | 4/2011 |
| CN | 102481230 | 5/2012 |
| (Continued) | | |

OTHER PUBLICATIONS

International Search Report and Written Opinion in International Application No. PCT/EP2016/076463, dated Feb. 10, 2017, 10 pages.

(Continued)

*Primary Examiner* — Bradley J Osinski
(74) *Attorney, Agent, or Firm* — Fish & Richardson P.C.

(57) ABSTRACT

A cartridge carrier assembly for a medicament delivery device comprises a cartridge carrier adapted to receive a cartridge defining a cavity containing a dose of a medicament, a needle hub being part of the cartridge carrier or coupled to the cartridge carrier such that the needle hub is fixed relative to the cartridge carrier, the needle hub adapted to receive a distal end or part of the cartridge, an injection needle having a tipped proximal needle section adapted to pierce a sealing element distally arranged on the cartridge, and a removable needle cap attachable to a distal end of the cartridge carrier. The needle hub comprises a cartridge retention feature adapted to abut the cartridge or a part (Continued)

thereof to limit axial movement of the cartridge in the distal direction such that the proximal needle section is spaced from the sealing element.

19 Claims, 4 Drawing Sheets

(51) Int. Cl.
  *A61M 5/32* (2006.01)
  *A61M 5/34* (2006.01)

(52) U.S. Cl.
  CPC ............ *A61M 5/32* (2013.01); *A61M 5/3202* (2013.01); *A61M 5/343* (2013.01); *A61M 2005/2073* (2013.01); *A61M 2005/247* (2013.01)

(56) References Cited

U.S. PATENT DOCUMENTS

| | | |
|---|---|---|
| 4,957,490 A | 9/1990 | Byrne et al. |
| 2012/0179109 A1 | 7/2012 | Takemoto et al. |

FOREIGN PATENT DOCUMENTS

| | | |
|---|---|---|
| CN | 102834132 | 12/2012 |
| CN | 102844065 | 12/2012 |
| CN | 103167887 | 6/2013 |
| CN | 103501842 | 1/2014 |
| CN | 106470719 | 3/2017 |
| EP | 0645156 | 3/1995 |
| EP | 2944340 | 11/2015 |
| EP | 2944341 | 11/2015 |
| JP | H07-51370 | 2/1995 |
| WO | WO 96/39213 | 12/1996 |
| WO | WO 2012/089620 | 7/2012 |

OTHER PUBLICATIONS

International Preliminary Report on Patentability in International Application No. PCT/EP2016/076463, dated May 8, 2018, 7 pages.

CARTRIDGE CARRIER ASSEMBLY

CROSS REFERENCE TO RELATED APPLICATIONS

The present application is the national stage entry of International Patent Application No. PCT/EP2016/076463, filed on Nov. 2, 2016, and claims priority to Application No. EP 15193195.3, filed in on Nov. 5, 2015, the disclosures of which are expressly incorporated herein in entirety by reference thereto.

TECHNICAL FIELD

The present disclosure generally relates to a cartridge carrier assembly for a medicament delivery device.

BACKGROUND

Administering an injection is a process which presents a number of risks and challenges for users and healthcare professionals, both mental and physical. Pre-filled syringes containing a selected dosage of a medicament for administering the medicament to a patient are known in the art. The pre-filled syringes include a hollow injection needle that is in fluid communication with the medicament stored in the cartridge. Due to a long-term storage of the pre-filled syringes, the injection needle can be clogged by the medicament, in particular by a medicament including monoclonal antibodies or an insulin. A clogged injection needle may lead to an increased injection time.

There remains a need for an improved cartridge carrier assembly for a medicament delivery device.

SUMMARY

An object of the present disclosure is to provide an improved cartridge carrier assembly for a medicament delivery device.

The object is achieved by a cartridge carrier assembly according to claim 1.

Exemplary embodiments are given in the dependent claims.

According to the present disclosure, a cartridge carrier assembly for a medicament delivery device comprises:
- a cartridge carrier adapted to receive a cartridge defining a cavity containing a dose of a medicament,
- a needle hub being part of the cartridge carrier or coupled to the cartridge carrier such that the needle hub is fixed relative to the cartridge carrier, the needle hub adapted to receive a distal end or part of the cartridge,
- an injection needle having a tipped proximal needle section adapted to pierce a sealing element distally arranged on the cartridge,
- a removable needle cap attachable to a distal end of the cartridge carrier, wherein the needle hub comprises a cartridge retention feature adapted to abut the cartridge or a part thereof to limit axial movement of the cartridge in the distal direction such that the proximal needle section is spaced from the sealing element, wherein the cartridge retention feature is deflectable by the cartridge allowing the cartridge to advance in the distal direction such that the proximal needle section pierces the sealing element, wherein the needle cap is adapted to prevent deflection of the cartridge retention feature when attached to the cartridge carrier. If the needle cap is removed, the cartridge retention feature is no longer prevented from being deflected by the cartridge so the cartridge can advance within the needle hub in order to allow the proximal needle section pierces the sealing element for establishing a fluid communication between the needle and the cavity within the cartridge. If the cartridge is biased in the distal direction relative to the cartridge carrier, needle insertion into the sealing element occurs automatically upon removal of the needle cap. The cartridge carrier assembly is thus particularly suitable as an emergency device or part thereof.

In an exemplary embodiment the cartridge retention feature is arranged within the needle hub and has the form of at least one radially inwardly directed protrusion or a series of circumferentially arranged radially inwardly directed protrusions or a circumferential rib adapted to abut the cartridge.

In an exemplary embodiment the cartridge retention feature is arranged in a resilient proximal section of the needle hub. The resilience of the proximal section may be achieved by a reduced wall thickness the proximal section or a part thereof relative to a wall thickness of the rest of the needle hub and/or by the proximal section comprising a resilient material and/or by providing one or more longitudinal slots in the proximal section.

In an exemplary embodiment a blocking feature is arranged on the needle hub substantially radially outwardly from the cartridge retention feature adapted to outwardly abut the needle cap. The blocking feature may have the form of at least one radially outwardly directed protrusion or a series of circumferentially arranged radially outwardly directed protrusions or an outwardly directed circumferential rib adapted to radially abut the needle cap. Likewise, the blocking feature may comprise an outer surface of the needle hub adapted to outwardly abut the needle cap.

In an exemplary embodiment a drive unit is arranged between a proximal end of the cartridge and the cartridge carrier biasing the cartridge in the distal direction. Thus, needle insertion into the sealing element occurs automatically upon removal of the needle cap.

In an exemplary embodiment the needle hub is adapted to receive the part of the cartridge being a ferrule, which may also be referred to as a crimp cap, arranged on the cartridge for holding the sealing element in position, wherein the cartridge retention feature is adapted to abut the ferrule.

In an exemplary embodiment the needle hub is adapted to seal against the needle cap when the cap is attached to the cartridge carrier. Thus, a distal needle section of the injection needle received within the needle cap may be maintained sterile.

In an exemplary embodiment the needle hub, in particular the proximal section thereof, is adapted to seal against the distal end or part of the cartridge received therein. Thus, the proximal needle section of the injection needle may be maintained sterile. The cartridge carrier assembly can thus be sterilized when the cap is attached to the distal end of the cartridge carrier and when the cartridge is inserted into the cartridge carrier and its distal end or part, in particular the ferrule, is received within the proximal section of the needle hub.

In an exemplary embodiment the needle hub comprises or consist of Polypropylene and/or Polyethylene. This may improve sealing of the proximal and/or distal needle section. Other material combinations are possible when the cartridge carrier consists of a two component molding, e.g. Polypropylene and a Thermoplastic Elastomere.

In an exemplary embodiment at least one sealing ring is arranged within the proximal section of the needle hub, the sealing ring adapted to seal against the distal end or part of the cartridge received therein, in particular the ferrule. This may improve sealing of the proximal needle section.

In an exemplary embodiment a sealing ring is arranged within the needle cap and/or on the needle hub to seal the needle cap against the needle hub. This may improve sealing of the distal needle section and minimize the friction force between the sealing components when the cartridge will be pierced.

In an exemplary embodiment the sealing ring comprises or consists of Polytetrafluoroethylene (PTFE). The PTFE sealing ring seals the respective interface during storage and transport. A PTFE sealing ring arranged within the proximal section of the needle hub also facilitates gliding of the ferrule and cartridge within the needle hub. This allows for advancing the cartridge by a less powerful drive element.

In an exemplary embodiment the injection needle further comprises a tipped distal needle section adapted to be covered by the needle cap.

In an exemplary embodiment the drive element comprises a coil spring.

In an exemplary embodiment an outer diameter of the ferrule substantially equals an outer diameter of a main body of the cartridge. This allows the cartridge main body to at least partially enter the needle hub after the ferrule has passed the cartridge retention feature.

The cartridge carrier assembly of the present disclosure may be applied with a conventional button or sleeve triggered medicament delivery device, e.g. an auto injector.

Further scope of applicability of the present disclosure will become apparent from the detailed description given hereinafter. However, it should be understood that the detailed description and specific examples, while indicating exemplary embodiments of the present disclosure, are given by way of illustration only, since various changes and modifications within the spirit and scope of the present disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

In the present application, when the term "proximal section/end" is used, this refers to the section/end of the cartridge carrier assembly, or the sections/ends of the components thereof, which under use of the cartridge carrier assembly is located the furthest away from the medicament delivery site of the patient. Correspondingly, when the term "distal section/end" is used, this refers to the section/end of the cartridge carrier assembly, or the sections/ends of the components thereof, which under use of the cartridge carrier assembly is located closest to the medicament delivery site of the patient.

Figure 1:
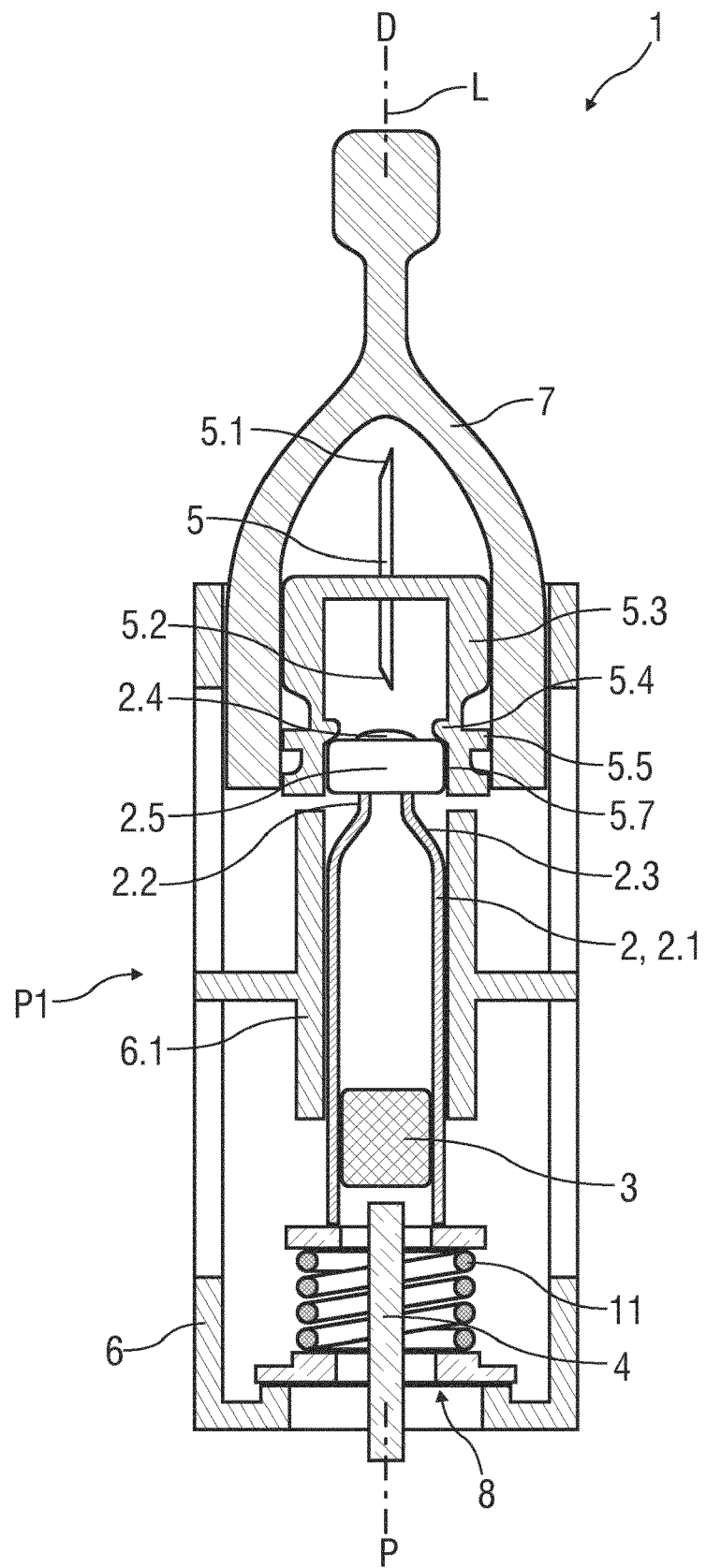
FIG. 1 is a schematic longitudinal section view of an exemplary embodiment of a cartridge carrier assembly according to the present disclosure in an initial position.

FIG. 1 is a schematic longitudinal section of an exemplary embodiment of a cartridge carrier assembly 1 for a medicament delivery device according to the present disclosure, whereby the cartridge carrier assembly 1 is in an initial position P1 as it would be presented to a user prior to use.

The cartridge carrier assembly 1 comprises a cartridge 2 forming a cavity that contains a dose of a medicament. The cartridge 2 may comprise a cylindrically shaped main body 2.1 and a neck section 2.2 on a distal end of the main body 2.1, wherein a shoulder 2.3 may connect the main body 2.1 and the neck section 2.2. The distal end of the cartridge 2 includes a flange to retain a sealing element 2.4, e. g. a fluid impermeable membrane, foil or septum, which is arranged across the open distal end of the cartridge 2. The sealing element 2.4 seals the medicament distally against environmental influences and ensures that the medicament remains within the cartridge 2. The sealing element 2.4 may be held in position on the cartridge 2 by a ferrule 2.5. An outer diameter of the ferrule 2.5 may equal or substantially equal an outer diameter of the main body 2.1.

The cartridge 2 is proximally limited by a bung 3 that is disposed within the cartridge 2 on a proximal end when the cartridge carrier assembly 1 is in the initial position P1. The bung 3 is arranged spaced from a piston rod 4. The piston rod 4 is adapted to displace the bung 3 within the cartridge 2 for ejecting the medicament from the cavity through an injection needle 5 that is arranged spaced from the cartridge 2 along a longitudinal axis L in a distal direction D when the cartridge carrier assembly 1 is in the initial position P1. In the context of the present application, the injection needle 5 may be suitable for intramuscular, subcutaneous, intradermal or transcutaneous injections.

The cartridge carrier assembly 1 comprises a cartridge carrier 6 comprising a sleeve 6.1 for receiving the cartridge 2.

A removable needle cap 7 is provided that covers and seals a distal needle section 5.1 of the injection needle 5.

The injection needle 5 comprises the distal needle section 5.1 and a proximal needle section 5.2 pointing towards and distally spaced from the sealing element 2.4 of the cartridge 2, when the cartridge carrier assembly 1 is in the initial position P1. The injection needle 5 is held in a needle hub 5.3 which in the initial position P1 is arranged within the needle cap 7. The needle hub 5.3 is part of the cartridge carrier 6 or coupled to the cartridge carrier 6 in such a manner that the needle hub 5.3 does not move with respect to the cartridge carrier 6. The cartridge carrier 6 may be connected to a body (not illustrated) of the cartridge carrier assembly 1.

The needle hub 5.3 comprises a cartridge retention feature 5.4 which may be arranged within the needle hub 5.3 and may have the form of at least one radially inwardly directed protrusion or a series of circumferentially arranged radially inwardly directed protrusions or a circumferential rib adapted to abut the ferrule 2.5 in order to maintain the spacing between the sealing element 2.4 and the tip of the proximal needle section 5.2. At least in a proximal section 5.7, where the cartridge retention feature 5.4 is arranged, the needle hub 5.3 is resilient so that the cartridge retention feature 5.4 can be outwardly deflected by the ferrule 2.5 in order to allow for advancing the cartridge 2 in the distal direction D such that the tip of the proximal section 5.2 can pierce the sealing element 2.4. The resilience of the proximal section 5.7 may be achieved by a reduced wall thickness the proximal section 5.7 or a part thereof relative to a wall thickness of the rest of the needle hub 5.3 and/or by the proximal section 5.7 comprising a resilient material and/or by providing one or more longitudinal slots in the proximal section 5.7.

A proximal face of the cartridge retention feature 5.4 may be ramped to facilitate its deflection by the ferrule 2.5. In the initial position P1 this outward deflection is prevented by a blocking feature 5.5 arranged on the needle hub 5.3 substantially radially outwardly from the cartridge retention feature 5.4. The blocking feature 5.5 may have the form of at least one radially outwardly directed protrusion or a series of circumferentially arranged radially outwardly directed protrusions or an outwardly directed circumferential rib adapted to radially abut the needle cap 7. Likewise, the blocking feature 5.5 may comprise an outer surface of the needle hub 5.3 adapted to outwardly abut the needle cap 7. The needle cap 7 is substantially cylindrically shaped in a proximal region receiving the needle hub 5.3. A more distal region may be tapered.

The cartridge carrier assembly 1 comprises a drive unit 8 that is arranged between a proximal end of the cartridge 2 and a proximal end of the cartridge carrier 6. In the present embodiment, the drive element 8 comprises a coil spring 11 that is coupled with its proximal end to the cartridge carrier 6, e.g. by a bayonet socket. Alternatively, the spring 11 may be coupled to the cartridge carrier 6 by any other suitable connection.

A distal end of the spring 11 is arranged on the proximal end of the cartridge 2, wherein the spring 11 is pre-stressed.

In an exemplary embodiment, the cartridge 2 may be a 1 ml or 1.5 ml standard cartridge.

Sterility of the distal needle section 5.1 may be provided by the dimensioning of an interface between the outer diameter of the needle hub 5.3 and the corresponding inner diameter of the needle cap 7. Sterility of the proximal needle section 5.2 may be provided by the dimensioning of an interface the outer diameter of the ferrule 2.5 and the corresponding inner diameter of the needle hub 5.3 and/or by an interface between the cartridge retention feature 5.4 and the ferrule 2.5. Sterility may be improved by appropriately selecting plastic materials of the needle hub 5.3 and the needle cap 7. In an exemplary embodiment, the needle hub 5.3 may comprise or consist of Polypropylene and/or Polyethylene and/or a Thermoplastic Elastomere. The Cap could also be moulded by a two component molding process, e.g. using Polypropylene and a Thermoplastic Elastomere.

Figure 2:
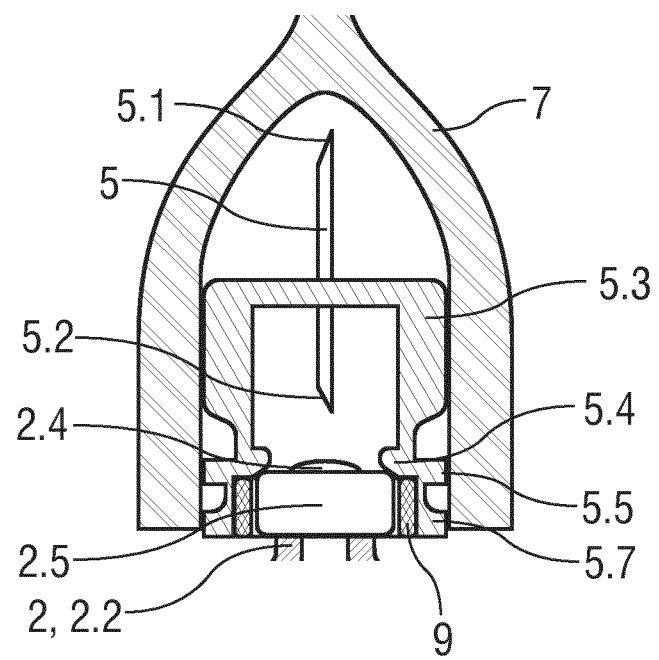
FIG. 2 is a schematic longitudinal section view of an exemplary embodiment of a cartridge carrier assembly according to the present disclosure in an operating position.
Figure 3:
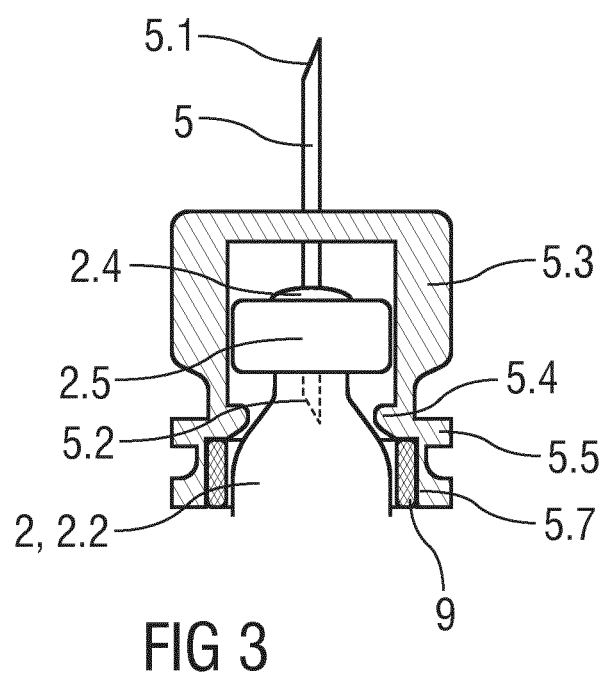
FIG. 3 is a schematic longitudinal section view of an alternative embodiment of a cartridge carrier assembly according to the present disclosure in an initial position.

FIG. 2 is a schematic detail view of an exemplary embodiment of the cartridge carrier assembly 1, in which a sealing ring 9 is arranged within a proximal section 5.7 of the needle hub 5.3, where the ferrule 2.5 is received. Likewise, a sealing ring 9 may be arranged within the needle cap 7 and/or on the needle hub 5.3 to improve sterility of the interfaces. In an exemplary embodiment the sealing ring 9 may comprise or consist of Polytetrafluoroethylene (PTFE). The PTFE sealing ring seals the respective interface during storage and transport. The PTFE sealing ring 9 arranged within the proximal section 5.7 of the needle hub 5.3 also facilitates gliding of the ferrule 2.5 and cartridge 2 within the needle hub 5.3. This allows for selecting a spring 11 with a reduced spring force. FIG. 3 is a schematic detail view of the cartridge carrier assembly 1 with the sealing ring 9 after removal of the needle cap 7 and after the cartridge 2 and the ferrule 2.5 have been advanced within the needle hub 5.3.

Figure 4:
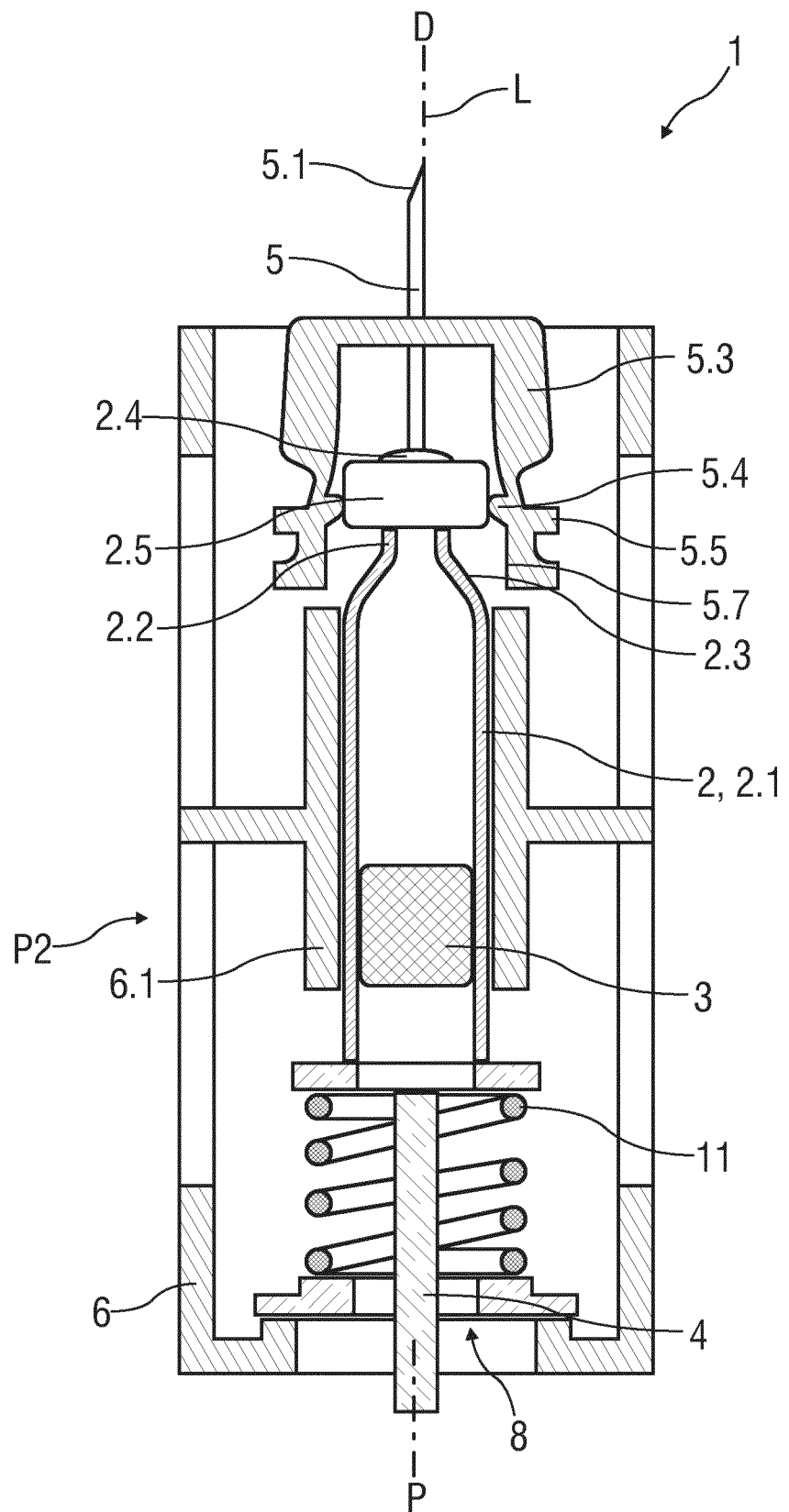
FIG. 4 is a schematic longitudinal section view of an alternative embodiment of a cartridge carrier assembly according to the present disclosure in an operating position.

FIG. 4 is a schematic longitudinal section of the cartridge carrier assembly 1 in an intermediate position P2. The needle cap 7 has been removed, i.e. pulled off in the distal direction D. Due to this removal the blocking feature 5.5 is no longer outwardly supported. The ferrule 2.5 thus outwardly deflects the cartridge retention feature 5.4 driven by the spring 11 and the cartridge 2 is advanced in the distal direction D such that the tip of the proximal section 5.2 of the needle 5 starts piercing the sealing element 2.4.

Figure 5:
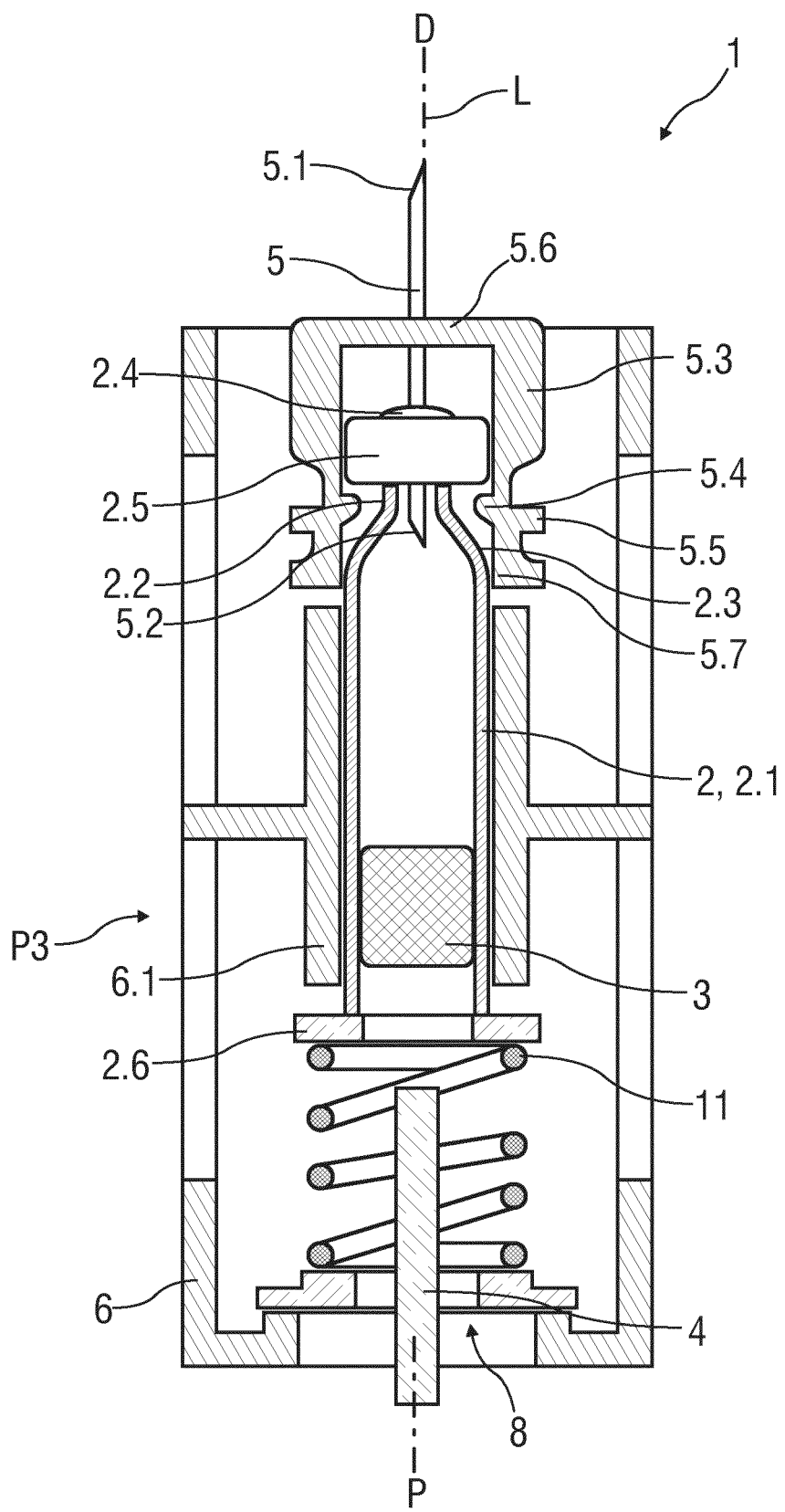
FIG. 5 is a schematic longitudinal section view of an alternative embodiment of a cartridge carrier assembly according to the present disclosure in an insertion position.

FIG. 5 is a schematic longitudinal section of the cartridge carrier assembly 1 in an insertion position P3. The ferrule 2.5 has advanced distally beyond the cartridge retention feature 5.4 and the neck section 2.2 and shoulder 2.3 of the cartridge 2 have entered the needle hub 5.3. The tip of the proximal section 5.2 of the needle 5 has fully pierced the sealing element 2.4 to establish a fluid communication between the needle 5 and the cavity within the cartridge 2. The cartridge 2 may arrive at an end position which may be defined by the shoulder 2.3 abutting the cartridge retention feature 5.4 and/or by the sealing element 2.4 or ferrule 2.5 abutting a distal end wall 5.6 of the needle hub 5.3, in which the needle 5 is held and/or by a proximal flange 2.6 of the cartridge abutting the sleeve 6.1 of the cartridge carrier 6.

Subsequently, a user may insert the needle into an injection site, e.g. a patient's skin, and initiate delivery of the medicament, e.g. by actuating a trigger button and/or a needle sleeve (not illustrated) when pushing the distal end of the cartridge carrier assembly 1 against the injection site. This actuation may then release a drive mechanism (not illustrated), e.g. a spring or motor, adapted to advance the plunger 4.

Since removal of the needle cap 7 causes the needle 5 to pierce the sealing element 2.4 in order to establish a fluid communication between the needle 5 and the cartridge 2, the cartridge carrier assembly 1 is suitable as an emergency medicament delivery device or a part thereof.

In an exemplary embodiment, the cartridge carrier assembly 1 may be assembled by the following steps:

The needle cap 7 is inserted into the cartridge carrier 6 in the proximal direction P. The cartridge 2 is inserted into the cartridge carrier 6 in the distal direction D until the ferrule 2.5 is located in the proximal section 5.7 of the needle hub 5.3. Both the distal needle section 5.1 and the proximal needle section 5.2 are thus sealed. The cartridge carrier assembly 1 may then be sterilized in a sterilizing unit, e.g. by application of heat. The cartridge carrier assembly 1 may be coupled to or inserted into a front subassembly or housing of medicament delivery device such as an auto-injector (not illustrated) and the drive unit 8 may be coupled to the proximal end of the cartridge carrier 6. The cartridge carrier assembly 1 thus arrives in the initial position P1 as illustrated in FIG. 1.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 cartridge carrier assembly
2 cartridge
2.1 main body
2.2 neck section
2.3 shoulder
2.4 sealing element
2.5 ferrule
2.6 flange
3 bung
4 piston rod
5 injection needle
5.1 distal needle section
5.2 proximal needle section
5.3 needle hub
5.4 cartridge retention feature
5.5 blocking feature
5.6 distal end wall
5.7 proximal section
6 cartridge carrier
6.1 sleeve
7 needle cap
8 drive unit
9 sealing ring
11 spring
D distal direction
L longitudinal axis
P proximal direction
P1 initial position
P2 intermediate position
P3 insertion position

The invention claimed is:

1. A cartridge carrier assembly for a medicament delivery device, the cartridge carrier assembly comprising:
   a cartridge carrier adapted to receive a cartridge defining a cavity containing a dose of a medicament,
   a needle hub being part of the cartridge carrier or coupled to the cartridge carrier such that the needle hub is fixed relative to the cartridge carrier, the needle hub adapted to receive a distal portion of the cartridge,
   an injection needle having a tipped proximal needle section adapted to pierce a sealing element distally arranged on the cartridge, and
   a removable needle cap attachable to a distal end of the cartridge carrier,
   wherein the needle hub comprises at least one protrusion directed radially inward and adapted to abut the cartridge or a part thereof to limit axial movement of the cartridge in a distal direction such that the proximal needle section is spaced from the sealing element,
   wherein the at least one protrusion is deflectable by the cartridge allowing the cartridge to advance in the distal direction such that the proximal needle section pierces the sealing element,
   wherein the needle cap is adapted to prevent deflection of the at least one protrusion when attached to the cartridge carrier, and
   wherein the needle hub is adapted to seal against the distal portion of the cartridge received therein.

2. The cartridge carrier assembly according to claim 1, wherein the needle hub further comprises a wall that defines an interior region of the needle hub, and wherein the at least one protrusion extends from an inner surface of the wall within the interior region of the needle hub.

3. The cartridge carrier assembly according to claim 2, wherein the at least one protrusion comprises a series of protrusions that are arranged circumferentially along the wall of the needle hub and directed radially inward.

4. The cartridge carrier assembly according to claim 2, wherein the at least one protrusion comprises a circumferential rib arranged along the wall of the needle hub and directed radially inward.

5. The cartridge carrier assembly according to claim 1, wherein the at least one protrusion is arranged along a resilient proximal section of the wall of the needle hub.

6. The cartridge carrier assembly according to claim 1, wherein the at least one protrusion is an at least one first protrusion, and wherein at least one second protrusion is arranged on the needle hub and directed substantially radially outward with respect to the at least one first protrusion to outwardly abut the needle cap.

7. The cartridge carrier assembly according to claim 6, wherein the at least one second protrusion is defined by an outer surface of the needle hub.

8. The cartridge carrier assembly according to claim 6, wherein the at least one second protrusion comprises a series of protrusions that are arranged circumferentially along a wall of the needle hub and directed radially outward.

9. The cartridge carrier assembly according to claim 6, wherein the at least one second protrusion comprises a circumferential rib arranged along a wall of the needle hub and directed radially outward.

10. The cartridge carrier assembly according to claim 1, further comprising a drive unit arranged between a proximal end of the cartridge and the cartridge carrier and biasing the cartridge in the distal direction.

11. The cartridge carrier assembly according to claim 10, wherein the drive unit comprises a coil spring.

12. The cartridge carrier assembly according to claim 1, wherein the needle hub is adapted to receive a ferrule arranged on the cartridge for holding the sealing element in position, wherein the at least one protrusion is adapted to abut the ferrule.

13. The cartridge carrier assembly according to claim 12, wherein an outer diameter of the ferrule substantially equals an outer diameter of a main body of the cartridge.

14. The cartridge carrier assembly according to claim 1, wherein the needle hub is adapted to seal against the needle cap when the cap is attached to the cartridge carrier.

15. The cartridge carrier assembly according to claim 14, wherein the needle hub comprises Polypropylene and/or Polyethylene.

16. The cartridge carrier assembly according to claim 14, wherein at least one sealing ring is arranged within a proximal section of the needle hub, the sealing ring adapted to seal against the distal portion of the cartridge received therein.

17. The cartridge carrier assembly according to claim 16, wherein a sealing ring is arranged within the needle cap and/or on the needle hub to seal the needle cap against the needle hub.

18. The cartridge carrier assembly according to claim 16, wherein the sealing ring comprises Polytetrafluoroethylene.

19. The cartridge carrier assembly according to claim 1, wherein the injection needle further comprises a tipped distal needle section adapted to be covered by the needle cap.

* * * * *

UNITED STATES PATENT AND TRADEMARK OFFICE
CERTIFICATE OF CORRECTION

PATENT NO. : 10,799,637 B2  
APPLICATION NO. : 15/773297  
DATED : October 13, 2020  
INVENTOR(S) : Michael Helmer Page 1 of 1

It is certified that error appears in the above-identified patent and that said Letters Patent is hereby corrected as shown below:

In the Specification

In Column 1, Line 9, after "filed" delete "in"

Signed and Sealed this  
Second Day of February, 2021

Drew Hirshfeld  
*Performing the Functions and Duties of the*  
*Under Secretary of Commerce for Intellectual Property and*  
*Director of the United States Patent and Trademark Office*